United States Patent [19]
Streicher

[11] Patent Number: 5,679,872
[45] Date of Patent: Oct. 21, 1997

[54] PROCESS FOR THE PURIFICATION OF AN ETHER COMPRISING TWO DISTILLATION STEPS

[75] Inventor: Christian Streicher, Rueil Malmaison, France

[73] Assignee: Institut Francais du Petrole, Rueil Malmaison, France

[21] Appl. No.: 433,765

[22] Filed: May 4, 1995

[30] Foreign Application Priority Data

May 4, 1994 [FR] France ............... 94 05657

[51] Int. Cl.$^6$ ............... C07C 43/00; C07C 41/00
[52] U.S. Cl. ............... 568/699; 568/697
[58] Field of Search ............... 568/697, 699

[56] References Cited

U.S. PATENT DOCUMENTS

| 5,158,652 | 10/1992 | Pucci et al. | 568/699 |
| 5,250,156 | 10/1993 | Pucci et al. | 203/14 |
| 5,348,624 | 9/1994 | Pucci et al. | 203/14 |

FOREIGN PATENT DOCUMENTS

| 0 497 680 A1 | 8/1992 | European Pat. Off. . |
| 0 507 076 A1 | 10/1992 | European Pat. Off. . |
| 0 542 596 A1 | 5/1993 | European Pat. Off. . |

Primary Examiner—Marianne M. Cintins
Assistant Examiner—Dwayne C. Jones
Attorney, Agent, or Firm—Pollock, Vande Sande & Priddy

[57] ABSTRACT

A process for the separation of a mixture of an ether, an alcohol and of hydrocarbons is described in which the mixture to be separated is introduced into a first distillation column from which almost all of the hydrocarbons are recovered overhead and the purified ether is recovered from the bottom; at least one phase is extracted as a side stream from the first distillation column and sent to a second distillation column from which the alcohol is recovered from the bottom and a mixture of alcohol, ether and hydrocarbons is recovered overhead and recycled to the first distillation column. This process is of particular use in separating mixtures of ethyl tertio-butyl ether (ETBE), ethanol and $C_4$ hydrocarbons.

23 Claims, 2 Drawing Sheets

PROCESS FOR THE PURIFICATION OF AN ETHER COMPRISING TWO DISTILLATION STEPS

FIELD OF THE INVENTION

The invention concerns the production of ethers from aliphatic monoalcohols containing at least two carbon atoms and from isoolefins containing at least four carbon atoms, in particular the production of ethyl tertio-butyl ether (ETBE).

STATE OF THE ART

Ethers such as ethyl tertio-butyl ether, or methyl tertio-butyl ether (MTBE) can be used as high octane number additives for unleaded or low lead petrols. ETBE can be added to petrols in concentrations of up to about 15% by volume, for example.

One production process for MTBE consists in carrying out an addition reaction between methanol and isobutene, contained for example in a $C_4$ cut from steam cracking or catalytic cracking. After reaction, the residual methanol is usually separated by azeotropic distillation with $C_4$ hydrocarbons and MTBE is readily obtained with a degree of purity which is suitable for addition to petrols.

Ethers can be produced from aliphatic monoalcohols containing at least two carbon atoms by an analogous process in which these alcohols replace the methanol. ETBE, for example, can thus be produced from ethanol and isobutene, also other ethers such as isopropyl tertio-butyl ether (IPTBE) from isopropanol and isobutene, or ethyl tertio-amyl ether (ETAE) from ethanol and isoamylenes. An example of this process for the synthesis of ETBE is described in "ETBE, un avenir pour l'éthanol" (translation: ETBE, a future for ethanol), by A Forestière, B Torck and G Pluche, given at the Conférence sur la Biomasse pour l'Energie et l'Industrie, Lisbon, 9–13 Oct. 1989, and in "MTBE/ETBE, an Incentive Flexibility for Refiners" by A Forestière et al., given at the "Conference on Oxygenated Fuels in Europe", London, 22–23 May 1990.

Contrary to the case of MTBE, however, after eliminating the $C_4$ hydrocarbons by azeotropic distillation (debutaniser) in this process, a large proportion of the residual ethanol is mixed with the ETBE product from the bottom of the debutaniser. The existence of an ethanol/ETBE azeotrope with 21% by weight of ethanol at atmospheric pressure, which boils at 66.6° C., makes it difficult to separate the ETBE with an adequate purity to satisfy regulations regarding concentrations of ethanol in petrol. Thus the ethanol content in ETBE must in general be between 0.1% and 10% by weight. Advantageously, the ETBE should be purified to less than 1% by weight of ethanol for it to be able to be added to petrol.

Thus, in order for ETBE to compete with MTBE as an additive which improves the octane number in unleaded petrol, the development of an economically attractive separation process would be particularly desirable.

A number of processes have been described for purifying the ETBE obtained from the bottom of the debutaniser.

French patent FR-B-2 683 523 describes a process in which the alcohol/ETBE extract obtained from the bottom of the debutaniser is washed with water and the water/alcohol mixture obtained is concentrated in a first distillation column then dehydrated in two further heteroazeotropic distillation columns using ETBE as the azeotroping agent. This process, however, is relatively complex and costly since it requires the use of 4 columns (1 washing column, 1 concentration column and 2 heteroazeotropic distillation columns). There is the additional drawback of producing water-saturated ETBE which is not of advantage as regards its use as an additive for petrol.

A simpler separation process for ethanol/ETBE mixtures has been described in French patent FR-B-2 672 048.

This process exploits the change in the composition of the azeotropic ethanol/ETBE mixture with pressure. The ethanol/ETBE mixture is thus separated using two distillation columns operating at two different pressures. Pure ETBE is thus obtained from the bottom of the first column operating at high pressure and pure ethanol is obtained from the bottom of the second column operating at low pressure. The azeotropic mixtures obtained overhead from each column are recycled to the other column.

French patent FR-B-2 673 624 describes a separation process for ethanol/ETBE mixtures by heteroazeotropic distillation using water as the azeotroping agent. Again, this process uses two distillation columns which can be operated at two different pressures and which respectively produce ethanol and pure ETBE at the bottom of each in analogous fashion to the process described above.

These two processes, however, require the use of two distillation columns which renders these processes relatively expensive as regards both investment and energy consumption. Further, as mentioned in French patent FR-B-2 672 048, the ethanol/ETBE mixtures obtained from the bottom of the debutaniser in ETBE synthesizing processes contain other impurities such as tertiary-butyl alcohol (TBA), diethyl ether (DEE), hydrocarbons containing at least 5 carbon atoms ($C_5$+), and ethyl 2-butyl ether (E2BE). Further, some of these impurities (DEE, $C_5$) are taken overhead from these distillation columns in the processes described in FR-B-2 672 048 and FR-B-2 673 624. Since the overhead products are completely recycled in these processes, these impurities accumulate gradually until they disturb the operation of the process and degrade the quality of separation, necessitating a purge overhead of one or other column to overcome this problem.

OBJECT OF THE INVENTION

An object of the present invention is thus to provide a process for the purification of ethers obtained from aliphatic monoalcohols containing at least two carbon atoms and isoolefins containing at least four carbon atoms, combining the azeotropic distillation step, which is normally present after the reaction section in ether synthesis processes, with a further distillation step to produce ether at the bottom of the azeotropic distillation column which is practically free of alcohol. The ether obtained can contain less than 1% by weight or even less than 0.1% by weight of residual alcohol.

The present invention particularly relates to a process for the purification of ETBE combining an azeotropic distillation step (debutaniser), normally present after the reaction section in ETBE synthesis processes, with a further distillation step, to obtain ETBE from the bottom of the debutaniser which is practically free of the alcohols (ethanol, TBA) present in the effluent from the reaction section. The ETBE obtained can contain less than 1% by weight, or even less than 0.1% by weight of residual alcohols.

The process of the present invention is applicable both when the azeotropic distillation step is constituted by a conventional distillation column and when this is a catalytic or reactive distillation step such as that described in "La distillation réactive: principe, applications et perspectives" (translation: Reactive Distillation: Principles, Applications and Perspectives), P Mikitenko, published in Pétrole et techniques, no.329, December 1986, p 34–38.

The present invention also relates to a process for the synthesis of an ether from an aliphatic monoalcohol containing at least two carbon atoms and an isoolefin containing at least four carbon atoms, including the ether purification process of the present invention, in which the alcohol is recycled to the reaction section or optionally to the catalytic or reactive distillation step when such a process is used.

The process of the present invention is particularly applicable to mixtures of ETBE, ethanol and $C_4$ hydrocarbons which constitute the effluents from the reaction sections from ETBE synthesis processes.

These mixtures generally contain 0.1% to 20% by weight, preferably 0.5% to 5% by weight, of ethanol and 5% to 80% by weight, preferably 10% to 50% by weight, of ETBE, the remainder being mainly constituted by hydrocarbons containing four carbon atoms ($C_4$). They also generally contain, as impurities, up to 1% by weight of water, up to 1% by weight of TBA, up to 1% by weight of DEE, up to 1% by weight of ethyl 2-butyl ether (E2BE), up to 5% by weight, preferably less than 1% by weight, of hydrocarbons containing at least 5 carbon atoms ($C_5+$) and up to 5% by weight of hydrocarbons containing 3 carbon atoms ($C_3$).

DESCRIPTION OF THE INVENTION

The mixture containing the ETBE, ethanol, the hydrocarbons ($C_4$) and impurities is introduced into the debutaniser. The debutaniser is operated at a pressure which is generally above atmospheric pressure, preferably between 5 and 15 bar. A distillate containing most of the $C_3$, $C_4$ and water from the mixture to be separated, a fraction of the ethanol and the $C_5+$ from the mixture to be separated, the distillate being practically free of other compounds (ETBE, E2BE, TBA, DEE), is recovered overhead. The majority of the ETBE and the other ethers (E2BE, DEE), along with a fraction of the $C_5+$ and small amounts (less than 1% by weight, preferably less than 0.1% by weight) of the alcohols (ethanol, TBA) are recovered from the bottom of the debutaniser.

At least one vapour, liquid or mixed phase is extracted as a side stream from the debutaniser and sent to a second distillation zone.

In accordance with an advantageous feature of the process, at least one phase is extracted as a side stream from at least one tray of the debutaniser where the ethanol concentration is substantially at a maximum.

In accordance with a further advantageous feature of the process, the second distillation zone is operated at a pressure which is lower than that of the debutaniser.

Thus the remainder of the ethanol contained in the mixture to be separated which is introduced into the debutaniser is recovered from the bottom of the second distillation zone, mixed with almost all of the TBA. The other products (ethers, hydrocarbons) are present only as impurities (less than 1% by weight in general). This alcohol mixture can then advantageously be recycled to the reaction section of an ETBE synthesis process.

A mixture of ethanol and ETBE is obtained overhead from the second distillation zone, along with varying proportions of other products (hydrocarbons, TBA, DEE, E2BE) which are recycled to the debutaniser. This mixture can advantageously be recycled to a tray in the debutaniser which is lower than or at the same level as that from which the side stream is extracted, preferably to a tray where the composition is substantially the same as that of the mixture.

Figure 1:
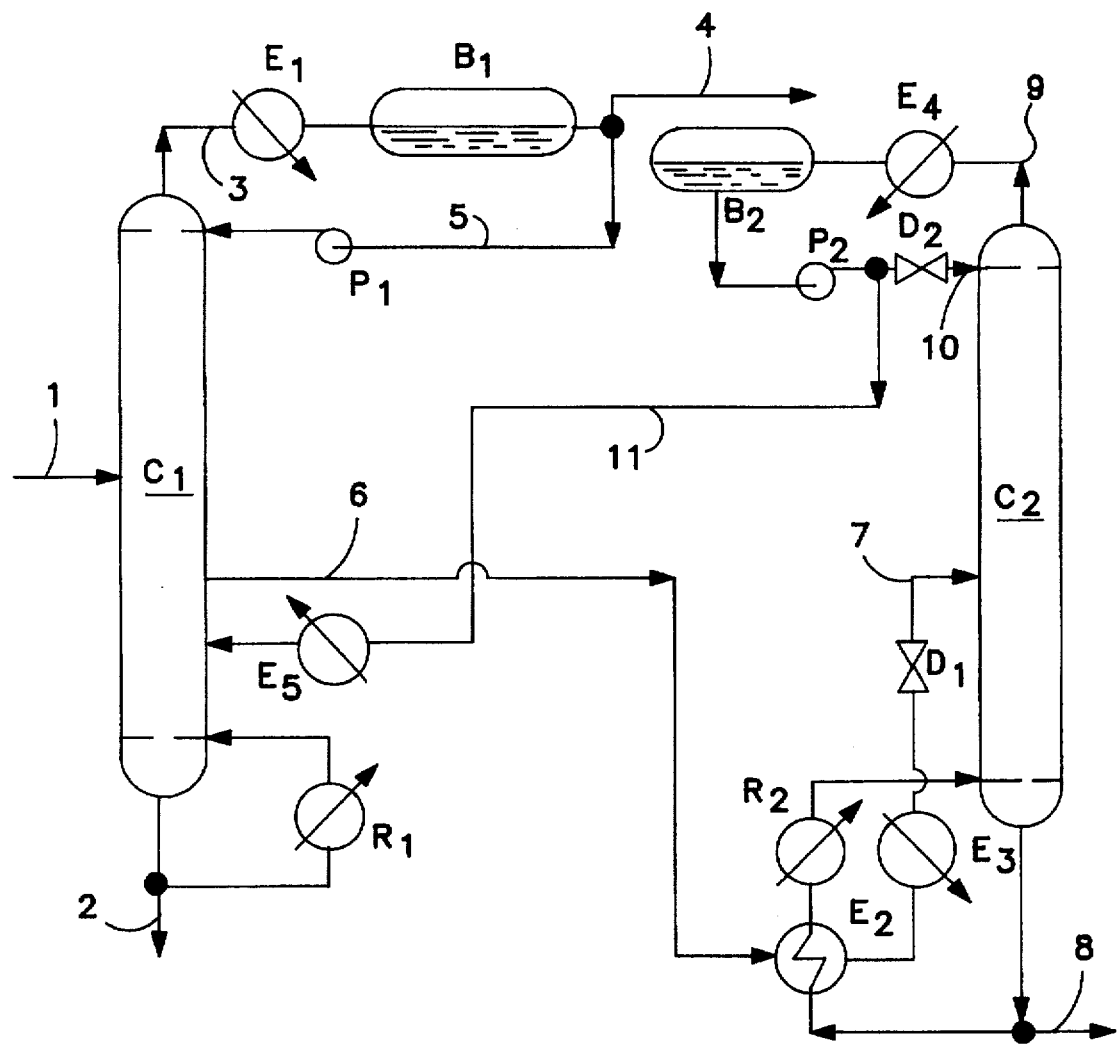
FIGS. 1 and 2 are schematic diagrams illustrating equipment suitable for carrying out the process of the present invention.

An advantageous embodiment of the invention will now be described with reference to FIG. 1.

The mixture to be separated is sent via line 1 to distillation column C1 (debutaniser). This column generally operates at a pressure p1 greater than 1 bar, preferably between 5 and 15 bar. It is heated by reboiler R1. The bottom temperature is generally between 70° C. and 200° C. The top temperature is generally between 30° C. and 100° C. The mixture to be separated is preferably introduced into debutaniser C1 at the bubble point at the pressure used to the tray with the closest composition possible to that of the mixture, for example to the central portion of the column in the case of mixtures containing 10% to 50% by weight of ETBE.

The product leaving the bottom of the debutaniser via line 2 is constituted by purified ETBE. Almost all of the ethers present in the mixture to be separated (ETBE and also E2BE and DEE) are thus recovered practically free of $C_3$, $C_4$ and water, with a $C_5+$ content which depends on that of the mixture to be separated, generally between 0.1% and 1% by weight, and with residual amounts of alcohols (ethanol and TBA) which depend on the operating conditions of the process, and are generally less than 1% by weight and even less than 0.1% by weight.

A vapour phase distillate constituted by $C_3$, $C_4$ and $C_5+$ hydrocarbons is recovered overhead from the debutaniser via line 3. It contains a variable proportion of ethanol, generally between 1% and 5% by weight, along with water at a concentration generally of less than 1% by weight, and is practically free of TBA and ethers (ETBE, E2BE, DEE).

This vapour phase is completely condensed and optionally undercooled in exchanger E1 then admitted into drum separator B1. From drum B1, a liquid distillate is recovered via line 4 which has the same composition and contains almost all the water and the $C_3$ and $C_4$ hydrocarbons from the mixture to be separated, along with a portion of the $C_5+$ hydrocarbons and the ethanol from the mixture to be separated. The remainder of the liquid recovered from drum B1 is sent via line 5 by means of pump P1, as a reflux to the top of debutaniser C1.

A fraction which is preferably gaseous is removed via line 6 as a side stream from debutaniser C1. This side stream is preferably extracted from the tray where the ethanol concentration in the gaseous phase is substantially at a maximum, in general from a tray which is lower than that at which the mixture to be separated is supplied to debutaniser C1. The mass flow rate of the removed gaseous fraction is an important operating parameter of the process. It must be adjusted as a function of the other operating parameters and the residual alcohol (ethanol, TBA) content required in the ETBE recovered from the bottom of debutaniser C1.

The gaseous fraction is then condensed at least partially in exchanger E2, optionally undercooled in exchanger E3, then depressurised to pressure p2 in pressure release valve D1 before being supplied via line 7 to distillation column C2, operating at pressure p2.

Pressure p2 is lower, in general by at least one bar, preferably 2 to 10 bar, than pressure p1 which is the operating pressure of the debutaniser. p2 is thus generally between 0.5 and 10 bar.

Column C2 can be heated at least in part by exchanger E2 (which recovers at least a portion of the heat of condensation of the vapour extracted via line 6), then by reboiler R2. The bottom temperature of column C2 is generally between 70° C. and 170° C., preferably between 80° C. and 120° C. The temperature at the top of column C2 is generally between 10° C. and 130° C., preferably between 35° C. and 70° C.

The product which leaves the bottom of column C2 via line 8 is a mixture of alcohols (ethanol, TBA), in varying proportions.

Depending on the operating conditions of the process, the alcohol mixture can have a residual ETBE content of less than 1% by weight, and even less than 0.1% by weight. It is practically free of all other products ($C_3$, $C_4$, $C_5$+, water, DEE and E2BE).

A vapour phase distillate containing varying proportions of ethanol, ETBE, $C_4$ and $C_5$+ hydrocarbons, TBA and DEE, is recovered overhead from column C2 via line 9. The distillate is entirely condensed and optionally undercooled in exchanger E4 then admitted to drum separator B2. The condensed distillate is recovered from drum B2 and brought by pump P2 to a pressure which is sufficient for it to be returned to debutaniser C1. A fraction of this distillate is returned, after depressurisation in valve D2, as a reflux to the head of column C2 via line 10. The remaining fraction of the distillate is then recycled via line 11 to debutaniser C1 where it is supplied after any necessary reheating and at least partial vaporisation in exchanger E5. The fraction recycled to debutaniser C1 is preferably supplied at the bubble point at the pressure used to the tray at which the liquid has the closest composition to the recycled fraction, generally to a tray which is lower than or at the same level as that from which the side stream is extracted. In the case where the recycled fraction is at least partially vaporised, it can be advantageous, after separating the vaporised fraction from the liquid fraction of the recycled fraction in a drum separator, to supply the vaporised fraction to debutaniser C1 at a tray which is higher than that at which the liquid fraction is admitted and optionally higher than that from which the side stream is extracted.

ADVANTAGES OF THE PROCESS

The process of the present invention has the main advantage of great simplicity as it can produce purified ETBE using a single distillation column in addition to the debutaniser present in all the processes previously described for the synthesis of ETBE. All the other processes previously described for purifying ETBE require the use of at least two columns in addition to the debutaniser. The process of the present invention is thus particularly economical as regards capital costs.

The process of the present invention has a further advantage of not allowing the impurities (TBA, $C_3$, $C_5$+, water, DEE, E2BE) to accumulate in the ethanol/ETBE/$C_4$ mixture to be separated, since these are eliminated with the different products from the process ($C_4$/ethanol mixture overhead from the debutaniser, ETBE from the bottom of the debutaniser and TBA/ethanol from the bottom of column C2). The process of the present invention does not therefore require a purge.

In a variation to the process of the invention, debutaniser C1 is replaced by a catalytic or reactive column C'1, meaning that the conversion rates of isobutene can be increased and/or the excess of ethanol used can be reduced. The effluents from column C'1 will have analogous compositions to those from debutaniser C1 simply with generally reduced ethanol contents.

The process for the purification of ETBE from a ETBE/ethanol/hydrocarbon mixture, as described above, can readily be integrated into a process for the synthesis of ETBE from ethanol and isobutene contained in a $C_4$ cut which can, for example, be sent from a steam cracking, catalytic cracking or butane dehydrogenation unit.

Figure 2:
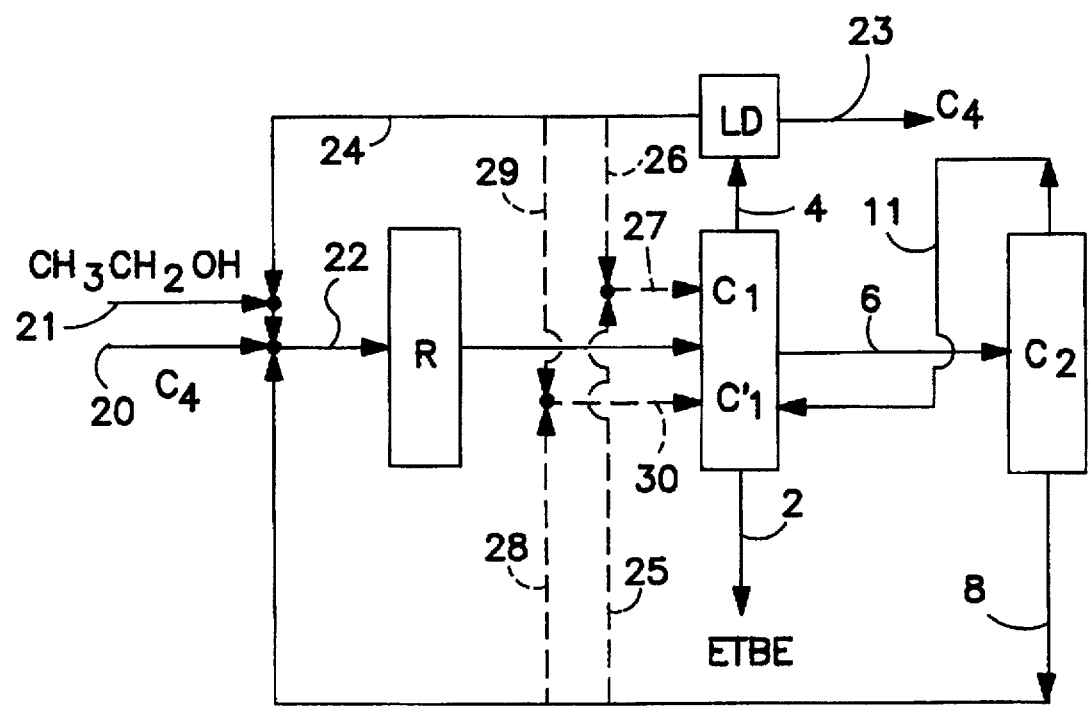

Such a process for the synthesis of ETBE will be described below with reference to FIG. 2. In FIG. 2, the various apparatus (pumps, heat exchangers, pressure reduction valves, drums . . . ), which are required for the different steps of the process to be operated, have not been shown.

The $C_4$ cut, containing isobutene and minor amounts of $C_3$ and $C_5$, is supplied via line 20 as a liquid. The ethanol which is added for the reaction is supplied via line 21 in the liquid phase. The water/ethanol azeotrope produced by section LD, which washes raffinate $C_4$ from debutaniser C1 (or C'1), is recycled as a liquid via line 24. The ethanol/TBA mixture produced at the bottom of distillation zone C2 of the process of the invention is recycled via line 8 in the liquid phase. These fluids are mixed then introduced into reaction section R via line 22.

The TBA present in the effluent from the reaction section results from the addition reaction of one molecule of water with one molecule of isobutene. The water is introduced into the reactor by recycling a water/ethanol azeotrope containing about 5% by weight of water from water washing section LD for the $C_4$ raffinate from debutaniser C1 (or C'1), but also because of its existence as a trace product in the added ethanol and in the $C_4$ cut supplied to the reaction zone. Finally, water is formed in the reaction section itself by the etherification of ethanol resulting in the formation of one molecule of water and one molecule of DEE from two molecules of ethanol.

Since the addition reaction leading to the formation of TBA is thermodynamically balanced, recycling the TBA with the ethanol produced at the bottom of distillation zone C2 to the reaction section limits the conversion of isobutene to TBA and thus increases the conversion of isobutene to ETBE, which is an advantage of the process.

A mixture constituted by ETBE, non reactive and unreacted $C_4$ hydrocarbons, excess unreacted ethanol and the various impurities mentioned above (TBA, water, $C_3$, $C_5$+, DEE, E2BE), is produced via line 1 from reaction section R. This mixture is supplied to debutaniser C1 (or C'1).

Purified ETBE is recovered from the bottom of debutaniser C1 (or C'1) via line 2, with traces of other ethers (DEE, E2BE), and hydrocarbons, water and a variable proportion of ethanol, generally 1% to 5% by weight, is recovered overhead. This raffinate, once liquefied, is introduced into water washing section LD via line 4.

This water washing section LD is in fact constituted by a water washing step per se producing practically ethanol-free hydrocarbons via line 23, also a water/ethanol mixture, and a distillation step for this mixture which produces water from the bottom which is recycled to the water washing section. An azeotropic water/ethanol mixture containing about 5% by weight of water is produced overhead and recycled via line 24 to reaction section R.

At least one vapour, liquid or mixed phase is extracted as a side stream from debutaniser C1 (or C'1) and supplied via line 6 to distillation zone C2.

Distillation zone C2 produces a mixture of ethanol, ETBE and other products overhead in varying proportions, which is recycled via line 11 to debutaniser C1 (or C'1). A mixture of ethanol and TBA is produced from the bottom and recycled via line 8 to reaction section R.

When debutaniser C1 is replaced by a catalytic or reactive distillation column C'1, it can be of advantage to recycle at least a portion of the ethanol/TBA mixture recovered from the bottom of distillation zone C2 to the catalytic or reactive distillation zone C'1 via lines 25 and 27. It can also be of advantage to recycle at least a portion of the azeotropic water/ethanol mixture produced by water washing section LD to the catalytic or reactive distillation column C'1, via lines 26 and 27. Line 27 can thus advantageously be disposed so that the recycled ethanol is supplied to one or more of the catalytic trays of C'1.

In some cases, it can be of advantage to recycle at least a portion of the azeotropic water/ethanol mixture produced by the water washing section LD via lines 29 and 30 and/or the ethanol/TBA mixture produced from the bottom of distillation zone C2 via lines 28 and 30, to debutaniser C1 (or C'1) and thus increase the concentration of ethanol at the tray of debutaniser C1 (or C'1) from which the side stream is extracted to supply C2 and thus facilitate the separation effected in distillation zone C2. Line 30 can thus advantageously be disposed so that the recycled ethanol is admitted close to the tray(s) from which the side stream is extracted.

Finally, the process of the present invention as described for the purification of ETBE can also be integrated into processes for the synthesis of other ethers from aliphatic monoalcohols containing at least two carbon atoms and isoolefins containing at least four carbon atoms, such as processes for the synthesis of IPTBE or ETAE.

The following example illustrates the invention.

EXAMPLE

A C$_4$/ethanol/ETBE mixture, representing an effluent from a reaction section in an etherification process, was separated to obtain the C$_4$ cut overhead of debutaniser (C1) containing less than 1 ppm by weight of ETBE, ETBE from the bottom of the debutaniser containing less than 0.1% by weight of residual ethanol, and an alcohol mixture (ethanol/TBA) from the bottom of distillation column C2 containing 0.1% by weight of ETBE.

The composition and the flow rate of the mixture to be separated, SUPPLY, are shown in the table below.

Debutaniser C1 was constituted by a stainless steel column with an internal diameter of 100 mm, containing 70 perforated baffle trays spaced 5 cm apart.

Distillation column C2 was constituted by a glass column with an internal diameter of 50 mm containing 30 perforated baffle trays spaced 5 cm apart.

The two columns were thermally insulated to prevent wall loss and each provided with an electrically heated boiler (R1 and R2 respectively), a cold water condenser (E1 and E4 respectively) and a reflux drum (B1 and B2 respectively). Column C2 was partially heated by the heat of condensation of the vapour extracted as a side stream from column C1, in an exchanger E2.

The trays in the distillation columns were numbered in increasing order from 1 at the top towards the bottom in each column.

Debutaniser C1 was operated at a pressure of 8.0 bar, measured at reflux drum B1. The temperature in column C1 ranged between 161.0° C. at the bottom and 67.5° C. at the top. The distillate obtained overhead from debutaniser C1 was condensed then undercooled: the temperature in reflux drum B1 was thus held at 50° C.

The mixture for separation, SUPPLY, was introduced in the liquid phase into debutaniser (C1) at tray 40 at a temperature of 76.4° C.

Mixture (HC) of distilled hydrocarbons was extracted as a liquid phase from reflux drum B1. The flow rate and the composition of this mixture HC are shown in the table below. The residual liquid fraction obtained from drum B1, with the same composition as mixture HC, was sent as a reflux to the top of debutaniser C1 at a flow rate of 3300 g·h$^{-1}$, representing a mass reflux ratio with respect to SUPPLY of 0.55.

A liquid ETBE phase with the other purified ethers, ETHER, was recovered from the bottom of the debutaniser. The flow rate and composition of product ETHER obtained are shown in the table below.

A liquid phase, EXTR, was extracted from tray 58 of debutaniser C1, at a temperature of 129.8° C. The flow rate and composition of this liquid phase are given in the table below.

This vapour phase was condensed in exchanger E2 then undercooled to a temperature of 58.8° C. in a cold water exchanger E3. This was then depressurised in pressure release valve D1 to the pressure in column C2 and admitted into this column at tray number 8.

Distillation column C2 was operated at a pressure of 1.1 bar, measured at reflux drum B2. The temperature in column C2 ranged from 93.9° C. at the bottom to 63.7° C. at the top. The temperature in the reflux drum B2 was 38.3° C.

A mixture (RECYC) was extracted as a liquid phase from reflux drum B2 and recycled, after bringing it to the pressure in debutaniser C1 and to a temperature of 117° C., to tray number 58 of debutaniser C1. The flow rate and composition of mixture RECYC are given in the table below.

The remaining liquid fraction obtained from drum B2, with the same composition as that of mixture RECYC, was sent as a reflux to the head of distillation column C2 as a flow rate of 2087 g·h$^{-1}$, representing a mass reflux ratio of 0.39 with respect to the supply (EXTR) to distillation column C2.

A mixture of alcohols (ALCS), essentially constituted by ethanol and TBA) was recovered as a liquid phase from the bottom of distillation column C2. The flow rate and composition are given in the table below.

TABLE

MATERIAL BALANCE IN PROCESS OF THE INVENTION

| BODY (wt %) | SUPPLY | ETHERS | HC | EXTR | RECYC | ALCS |
|---|---|---|---|---|---|---|
| C3 | 1.24 | <1 ppm | 1.82 | <1 ppm | <1 ppm | <1 ppm |
| C4 | 64.87 | 0.02 | 94.85 | 5.61 | 5.77 | <1 ppm |
| C5+ | 1.00 | 1.04 | 1.01 | 24.22 | 24.93 | <1 ppm |
| Water | 0.14 | <1 ppm | 0.20 | <1 ppm | <1 ppm | <1 ppm |
| Ethanol | 3.72 | 0.10 | 2.11 | 18.08 | 16.02 | 88.46 |
| TBA | 0.29 | 0.01 | 28 ppm | 0.54 | 0.22 | 11.44 |
| ETBE | 28.63 | 98.50 | <1 ppm | 49.24 | 50.68 | 0.10 |
| DEE | 0.05 | 0.13 | 77 ppm | 2.31 | 2.38 | <1 ppm |
| E2BE | 0.06 | 0.20 | <1 ppm | <1 ppm | <1 ppm | <1 ppm |
| Flow Rate (g/h$^{-1}$) | 6000 | 1744 | 4104 | 5352 | 5200 | 152 |

I claim:

1. A process for the purification of an ether formed from an aliphatic monoalcohol containing at least two carbon atoms and an isoolefin containing at least four carbon atoms, from a mixture containing said ether, said monoalcohol and hydrocarbons containing the same number of carbon atoms as that in said isoolefin, said process being characterised in that it comprises the following steps:

(a) introducing said mixture into a first distillation zone, from which almost all of the hydrocarbons are recovered overhead and the purified ether is recovered from the bottom;

(b) extracting at least one phase as a side stream from said first distillation zone and sending it to a second distillation zone, operating at a lower pressure to that of said first distillation zone, from which purified monoalcohol is recovered from the bottom and a mixture of monoalcohol, ether and hydrocarbons is recovered as an overhead effluent and recycled to said first distillation zone.

2. A process according to claim 1, in which a mixture of ethyl tertio-butyl ether (ETBE) and ethanol which also contains at least $C_4$ hydrocarbons is treated, said process being characterised in that it comprises the following steps:

(a) introducing the mixture to be separated into a first distillation zone, the debutanising zone, from which almost all of the $C_4$ hydrocarbons are recovered overhead and the purified ETBE is recovered from the bottom;

(b) extracting at least one phase as a side stream from said first distillation zone and sending it to a second distillation zone, operating at a lower pressure to that of said first distillation zone, from which purified ethanol is recovered from the bottom and a mixture of ethanol and ETBE and hydrocarbons is recovered as an overhead effluent and recycled to said first distillation zone.

3. A process according to claim 2, characterised in that the side stream is extracted from said first distillation zone from at least one tray in which the alcohol concentration is substantially at a maximum.

4. A process according to claim 2, characterised in that the condensed overhead effluent from said second distillation zone is recycled at least in part, if necessary after reheating, to the first distillation zone to a tray thereof which is located below (or at the same level as) the tray at which extraction is effected.

5. A process according to claim 2, characterised in that the portion of the condensed overhead effluent from the second distillation zone which is recycled to the first distillation zone is reheated and partially vaporised, a liquid fraction and a vapour fraction are separated, said liquid fraction is admitted to the first distillation zone at a tray thereof which is below (or at the same level as) the tray at which extraction is effected; and said vapour fraction is admitted to said first distillation zone at a tray which is located above that at which said liquid fraction is admitted.

6. A process according to claim 2, characterised in that the second distillation zone is operated at a pressure which is at least 1 bar lower than that at which said first distillation zone is operated.

7. A process according to claim 2, characterised in that, in step (a), the first distillation zone is operated at a pressure which is above atmospheric pressure at a bottom temperature of 70° C. to 200° C., at a top temperature of 30° C. to 100° C., the mixture to be separated is introduced into said distillation zone to the tray with the closest composition to that of said mixture; and in that, in step (b), the phase to be sent to the second distillation zone is extracted from a tray in said distillation zone which substantially corresponds to the maximum ethanol concentration, and it is depressurised to the pressure of the second distillation zone of 0.5 to 10 bar, the bottom temperature of said second distillation zone being 70° C. to 170° C. and the top temperature being 10° C. to 130° C.

8. A process according to claim 7, characterised in that in step (b), said extracted phase is a vapour phase extracted from the tray in said first distillation zone where the ethanol concentration in the vapour phase is substantially at a maximum, and it is at least partially condensed before admission into said second distillation zone.

9. A process according to claim 8, characterised in that at least a portion of the heat of condensation of the vapour phase extracted from the first distillation zone is used to heat, at least in part, the second distillation zone.

10. A process according to claim 2, characterised in that the mixture to be separated is from an etherification zone reacting isobutene and ethanol to synthesize ETBE.

11. A process according to claim 10, characterised in that the ETBE/ethanol mixture to be separated contains 0.1% to 20% by weight of ethanol and 5% to 80% by weight of ETBE, the remainder being principally constituted by $C_4$ hydrocarbons, and proportions of up to 1% by weight of water, up to 1% by weight of tertiary butyl alcohol (TBA), up to 1% by weight of diethyl ether (DEE), up to 1% by weight of ethyl 2-butyl ether (E2BE), up to 5% by weight of hydrocarbons containing at least 5 carbon atoms ($C_5$+) and up to 5% by weight of $C_3$ hydrocarbons.

12. A process according to claim 11, characterised in that, in step (a), the overhead effluent from the first distillation zone comprises the major portion of $C_3$ and $C_4$ hydrocarbons, the major portion of the water, a fraction of the ethanol and $C_5$+ hydrocarbons, and the mixture to be separated and is substantially free of ETBE, E2BE, TBA and DEE; the bottom effluent from said first distillation zone comprises, apart from purified ETBE, the major portion of the E2BE, a portion of the DEE, a fraction of the $C_5$+ hydrocarbons and less than 1% by weight of the ethanol and the TBA; and the bottom effluent from the second distillation zone essentially consists of ethanol and TBA.

13. A process according to claim 2, characterised in that the purified ETBE recovered from the bottom of the first distillation zone contains less than 0.1% by weight of alcohol(s).

14. A process according to claim 2, characterised in that the purified ETBE recovered from the bottom of the first distillation zone contains less than 0.1% by weight of alcohol(s).

15. A process according to claim 1 for the purification of an ether, formed from an aliphatic monoalcohol containing at least two carbon atoms and an isoolefin containing at least four carbon atoms, from a mixture containing said ether, said monoalcohol and hydrocarbons containing the same number of carbon atoms as that in said isoolefin, said process further comprising the steps of integrating said purification with a process for the synthesis of an ether in such a way that said mixture from which said ether is to be separated is effluent from a reaction section of said synthesis of said ether and said monoalcohol obtained from the bottom of the second distillation zone is returned to said reaction section.

16. A process according to claim 2 for the purification of ETBE from a mixture comprising ETBE, ethanol and at least $C_4$ hydrocarbons, said process further comprising the steps of:

conveying the overhead vapor phase effluent from the first distillation zone, after condensing, to a water washing section, to produce an effluent, constituted by hydrocarbons that are essentially free of ethanol, and a water/ethanol mixture;

separating said water/ethanol mixture by distillation into a water bottoms product which is recycled to the washing section and an azeotropic water/ethanol mixture containing about 5% by weight of water;

mixing a $C_4$ cut stream containing minor proportions of $C_3$ and $C_5$+ hydrocarbons and additional ethanol, said water/ethanol azeotrope from said washing section, and a bottom effluent from said second distillation zone into a reaction section recycle stream;

admitting said reaction section recycle stream into a reaction section which operates under conditions suitable for the etherification of isobutene and ethanol;

supplying to the first distillation zone an effluent from the reaction section as the mixture to be separated in the first distillation zone which comprises ETBE, non reactive or unreacted $C_4$ hydrocarbons, excess ethanol and various impurities including TBA, water, $C_3$ and $C_5+$ hydrocarbons, DEE and EZBE.

17. A process according to claim 16, wherein the distillation zone is a catalytic or reactive distillation zone.

18. A process according to claim 17, wherein at least a portion of the bottom effluent from the second distillation zone is recycled to said catalytic or reactive distillation zone, to a tray corresponding to a catalytic tray.

19. A process according to claim 17, wherein at least a portion of the azeotropic water/ethanol mixture produced by the washing-distillation zone is recycled to said catalytic or reactive distillation zone, to a level corresponding to a catalytic tray.

20. A process according to claim 16 wherein at least a portion of the effluent from the bottom of the second distillation zone is recycled to said distillation zone, to a level close to that at which the extraction is made from said zone.

21. A process according to claim 16 wherein at least a portion of the azeotropic water/ethanol mixture produced by the washing-distillation zone is recycled to said distillation zone, to a level close to that at which the extraction is made from said zone.

22. A process according to claim 6 wherein said second distillation zone is operated at pressure 2 to 10 bars lower than that of which said first distillation zone is operated.

23. A process according to claim 7 wherein said first distillation zone is operated at a pressure between 5 and 10 bar.

* * * * *